United States Patent [19]

Frenzel

[11] 4,433,060

[45] Feb. 21, 1984

[54] CHEMILUMINESCENT IMMUNOASSAYS WITH TRIPHENYLMETHANE DYES ACTIVATED BY $H_2O_2$ AND A CHLORAMINE

[76] Inventor: Bernd Frenzel, Spitzelbergstrasse 18a, 8000 München 71, Fed. Rep. of Germany

[21] Appl. No.: 267,414

[22] Filed: May 26, 1981

[30] Foreign Application Priority Data

Dec. 22, 1980 [DE] Fed. Rep. of Germany ....... 3048447
Feb. 20, 1981 [DE] Fed. Rep. of Germany ....... 3106444

[51] Int. Cl.³ .................... G01N 33/54; G01N 33/58; G01N 33/52
[52] U.S. Cl. .................... 436/518; 436/536; 436/546; 436/800; 436/820
[58] Field of Search ............ 424/8, 12; 23/230 B; 436/536, 546, 800, 820, 518

[56] References Cited

U.S. PATENT DOCUMENTS 4,104,029 8/1978 Maier ................. 23/230 B
4,238,195 12/1980 Boguslaski ............ 23/230 B

*Primary Examiner*—Sidney Marantz
*Attorney, Agent, or Firm*—Oblon, Fisher, Spivak, McClelland & Maier

[57] ABSTRACT

Process for the quantitative and qualitative determination of antigens, antibodies and their complexes by means of a chemiluminescing labelling substance activated or excited to chemiluminescence by an analytical reagent. By means of a serological reaction, initially an antigen/antibody complex is formed which is treated with a chemiluminescing conjugate containing chemiluminescing triphenylmethane dyes and the chemiluminescence of the chemiluminescing complex formed is measured. Qualitative or quantitative details on the substances to be measured are obtained on the basis of the resulting measured values. The dye labels are activated by either hypochlorites or mixtures of $H_2O_2$ and a chloramine.

7 Claims, 1 Drawing Figure

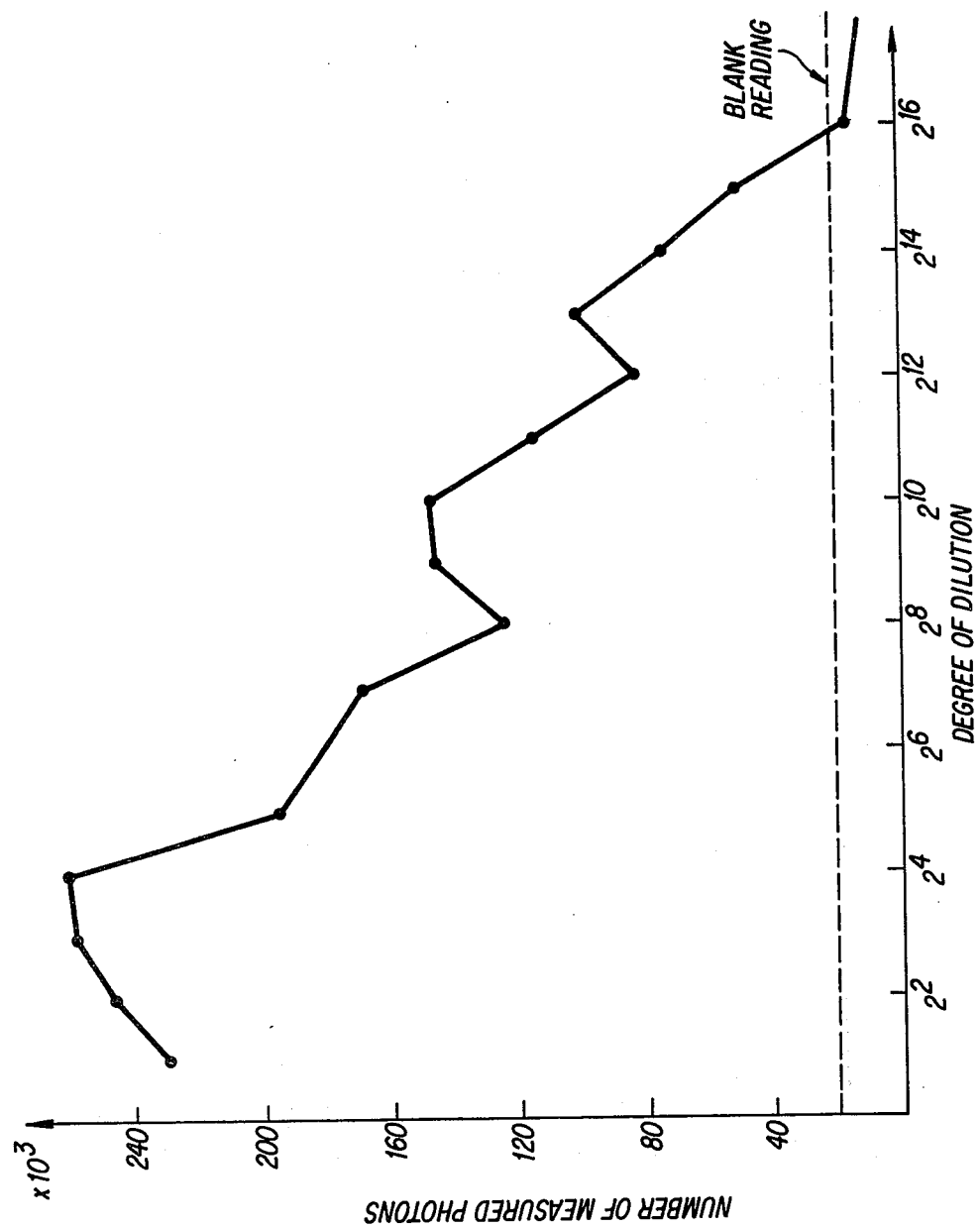

CHEMILUMINESCENT IMMUNOASSAYS WITH TRIPHENYLMETHANE DYES ACTIVATED BY $H_2O_2$ AND A CHLORAMINE

BACKGROUND OF THE INVENTION

The invention relates to a process for the quantitative and qualitative determination of antigens, antibodies and their complexes by means of a chemiluminescing labelling substance excited to a chemiluminescence by an analytical reagent, as well as to the use of chemiluminescing triphenylmethane dyes for performing such a process.

It is very important to be able to measure antigens, antibodies or their complexes in secretions, excretions and body fluids of both vertebrate and human organisms. In this way, it is possible inter alia to obtain diagnostic information.

It is known to detect a serological reaction by labelling one or more reaction components with a radioactive isotope by conjugating with an enzyme, a fluorescent dye or a chemiluminescent such as luminol or luciferin.

The radioimmunoassay is described in the Journal Clinical Endocrinology 27, 1967, p.973 and loc.cit. 28, 1968, p.343. The important disadvantage of this assay is that it is necessary to use radiation-emitting isotopes, whilst complicated and costly equipment is required for carrying out such an assay.

When labelling a reaction component with an enzyme, the disadvantage is that it is a complicated procedure to carry out this labelling and the reaction product obtained is difficult to store and use. In addition, the enzymes to be used are biologically active substances of an extremely complex nature, this being the cause of the aforementioned difficulties. In addition, the substrates used for detecting the combined enzyme are carcinogenic, which is disadvantageous. The enzyme assay of this type is described in the Bull.World Health Organ 53, 1976.

In the fluorescence method, a reaction product containing antigens and antibodies is identified by fluorescence, accompanied by irradiation with short-wave light. It is disadvantageous in this connection that the excitation light must be separated from the emitted light by costly equipment.

The chemiluminescents hitherto used for chemiluminescence have been difficult to bond to the reactants of a serological reaction and besides this they lose up to 99.3% of their original luminescence after bonding, cf e.g. Nature, Vol.299, 1979, pp.646-647. It is also reported in the Journal of Immunological Methods 21, 1978, pp.178-184 that the chemiluminescent luminol is for this reason unsuitable for routine clinical laboratory tests.

BRIEF SUMMARY OF THE INVENTION

The problem of the invention is in particular to improve the aforementioned process in such a way that antigens, antibodies or their complexes can be detected simply, precisely and in a highly sensitive qualitative or quantitative manner, whilst proposing chemiluminescing labelling substances particularly suitable for performing this process.

According to the invention, this problem is solved in that (a) by means of a serological reaction an antigen/antibody complex is formed and is then separated, the separated antigen/antibody complex is then treated with a chemiluminescing conjugate containing a chemiluminescing labelling substance in the form of chemiluminescing triphenylmethane dyes which can be coupled alone or by using additional substances to antigens, antibodies and their complexes and a chemiluminescing complex to be measured is formed, or (b) by means of a serological reaction between a chemiluminescing conjugate and an antigen or antibody, a chemiluminescing complex to be measured is directly formed and the chemiluminescing complex formed in each case is separated and after adding the exciting analytical reagent, the chemiluminescence is measured and on the basis of the measured values qualitative or quantitative information is obtained on the antigens, antibodies or their complexes.

According to the invention, chemiluminescing triphenylmethane dyes can be used with particular advantage for the quantitative and qualitative determination of antigens, antibodies and their complexes.

When the invention refers to antigens and antibodies, these terms are to be understood in the widest sense. Antigens are substances which lead to the formation of antibodies after introduction into the organism of humans and animals. Antigens are animal and vegetable proteins foreign to the species and particularly those of fomes, as well as many substances of a complicated nature with a fatty, saccharide (or sugar), amine and azo-like structure. These can be substances e.g. conjugated proteins, proteins, polysaccharides, lipids or nucleic acids leading to the formation of antibodies in the organism of vertebrates and humans and which specifically react therewith. These also include haptens in general and which are also termed "incomplete antigens" which, due to their limited size cannot in themselves lead to the formation of antibodies, but can form a specific bond with the corresponding antibodies. Antigens can be e.g. viruses, bacteria or fungi or parts thereof and the term antigen also covers e.g. certain hormones, vitamins, enzymes or medicaments. In connection with the definition of the terms "antigens" and "antibodies" reference is made to Kabat "Einführung in die Immunchemie und Immunologie", Springer Verlag, 1971, pp.9-25 and 143-197.

Within the meaning of the invention, antibodies are specific products of the immune response formed in the vertebrate or human organism after antigen contact and which can specifically react with the antigen. The term antibody also covers certain bonding proteins, which can specifically be bonded to one or more substances such as e.g. antibodies. An example is protein A. Of particular importance are the antibodies formed by immunoglobulins of class IgG, IgM, IgA and IgE. They are described in detail in Kabat "Einführung in die Immunchemie und Immunologie", Springer Verlag, 1971, pp.143-197.

The process according to the invention is particularly important in the detection and identification of antigens and antibodies in viral and bacterial illnesses. Particular importance is attached to the detection of the surface antigen of hepatitis B virus. It can also be used with particular advantage in the detection of antibodies against hepatitis, measles and rubella viruses.

It has been found that chemiluminescing triphenylmethane dyes can be advantageously used as the chemiluminescing labelling substance according to the invention. They can in particular be constituted by amino and hydroxytriphenylmethane dyes, together with phthaleins and derivatives of these compound groups. According to the invention, the chemiluminescing triphenylmethane dyes must in each case be suitable for coupling with antigens, antibodies and their complexes, either alone or by using additional substances.

Among the triphenylmethane dyes, preference is given to the group of phthaleins and their derivatives. Fluorescein and derivatives thereof can be used with particular advantage. This advantage is very apparent when those fluorescein derivatives are used which can be bonded particularly well to conjugated proteins or proteins. This means that the fluorescein is substituted with one or more groups aiding the affinity thereof with respect to the coupling with the indicated antigens and antibodies. The isothiocyanate and the isocyanate group is particularly advantageous as the coupling-providing or coupling-aiding substituent.

Fluorescein may, in addition to the coupling-aiding or providing substituents also non-coupling substituents, which also applies to all other triphenylmethane dyes which can be considered, can acquire a coupling capacity or have the latter improved by adding a suitable reagent, which brings about a coupling reaction or bridging between the triphenylmethane parent substance and the particular antigen or antibody or equivalents thereof.

When reference is made in the present invention to the "coupling capacity", this is to be understood in its widest sense. In no case is it intended that it be limited to a specific bonding type. It is in fact only intended to show that a complex or a complex-like structure results from an interaction of the indicated reactance in any form.

In individual cases, it is conceivable that the antigen to be labelled cannot or cannot adequately react with the particular chemiluminescing labelling substance used. In such cases, standard conjugated proteins or proteins are used, which are initially bonded to the antigen, so that subsequently the labelling substance can be bonded to the protein of the resulting reaction product. The reverse procedure can also be adopted by initially bonding the labelling substance to the conjugated protein or protein and then correlating such a conjugate with the antigen in question.

For exciting or activating the chemiluminescing labelling substance to be used according to the invention, it is fundamentally possible to use those substances which react with the labelling substance in such a way that it emits photons. In most cases, the chemiluminescence of the labelling substance to be used according to the invention can be attributed to an oxidation process in which oxygen, particularly free oxygen acts on the substrate. This oxygen can be made to act directly or on the basis of a preceding chemical reaction. The exciting or activating substances contained in the analytical reagent for chemiluminescence include inter alia hydrogen peroxide, ozone, salts of halogen oxacids, particularly hypochlorite such as sodium hypochlorite, permanganates, chromates, iron hexacyanoferrate (III), salts with oxidizing metal ions such as cations, e.g. copper (II) and cerium (IV) ions and the like, peroxidases, chloramine, etc. Particular preference is given to hypochlorites, preferably sodium hypochlorite as well as chloramine in conjunction with hydrogen peroxide. Activating or exciting analytical reagents usable according to the invention are particularly described in analytical chemistry, Vol.50, No.8, July 1978.

As will be apparent to the Expert, the process of the invention can be realized in many different ways. Firstly and in per se known manner, the antigen/antibody complex must be formed as a result of a serological reaction. This can take place in various ways in that initially either the antigen and antibody are present in a solution, or one of them, i.e. the antigen or the antibody is bonded to a solid phase. Reference is made in this connection to a liquid or solid phase assay. At the end of the serological reaction, in both cases the antigen/antibody complex is separated from the remaining reaction medium. In the solid phase assay, this can take place in simple manner by decanting the supernatant liquid, optionally after centrifuging. In the liquid phase assay, separation takes place e.g. by centrifuging with subsequent decanting or filtering, particularly ultrafiltration, chromatography and the like.

The antigen/antibody complex separated in this or in some similar manner is subsequently brought into contact with a liquid medium containing the chemiluminescing conjugate to be interacted therewith.

The chemiluminescing conjugate contains one of the aforementioned chemiluminescing triphenylmethane dyes, as well as the antigen or antibody (or protein). A new chemiluminescing complex separated e.g. by means of one or more of the aforementioned separation methods is formed from the chemiluminescing conjugate and the antigen/antibody complex. In this connection, it can already be present in the measuring cell, can be formed therein or is transferred thereinto. In each case, prior to performing the measurement, the exciting analytical reagent is added, it being unimportant in what type of solvent it is present, if such a solvent is required. However, preference is given to an aqueous medium containing the exciting or activating substance. It has proved advantageous to work in an alkaline range. From the practical standpoint, it is advantageous to use a sodium hypochlorite solution, whose concentration in aqueous solution is adjusted in such a way that there are 6 to 48 g of active chlorine per liter.

Hereinbefore, a process has been described in which the chemiluminscing labelling substance is "indirectly" bonded to the reactance present. However, it is also possible to use a "direct" assay. For this, either an antigen or antibody is introduced beforehand and as a function of said substance an antibody or antigen conjugate (with a chemiluminescing labelling substance) is added and a chemiluminescing complex formed, which is subsequently separated. This is followed by the previously described chemiluminescence measurement after adding the exciting analytical reagent.

The process according to the invention can be carried out with particular advantage on the basis of a sandwich assay. A sandwich assay can be fundamentally employed within the scope of a liquid or a solid phase assay. The essential characteristic of a conjugate formed during a sandwich assay is that in the complex to be measured with respect to the chemiluminescence the reactant to be detected has reacted in the form of an antigen or an antibody both with its conjugated and its non-conjugated reactant. On ignoring the coupled labelling substance, it is a symmetrically formed complex in which the central reaction component is the antigen or antibody which is to be detected or identified. Thus, the reaction component introduced beforehand interacts on two sides of this central reaction component.

The chemiluminescence can be measured with commercial photometers. The procedure can be such that a calibration curve is plotted with predetermined, known quantities of antigen and antibody. Values determined with an unknown substance (either an antigen or an antibody) are then quantitatively evaluated on the basis of the calibration curve.

However, it is also possible, although this is to be considered under semiquantitative standpoints, to make a comparison regarding the sensitivity with other known determination methods. In most fields of application, radioimmunoassay, which has hitherto been considered as particularly detection sensitive, but which has the aforementioned disadvantages has an inferior sensitivity to the process of the invention. Thus, e.g. the antibody titre of a hyperimmunoserum with respect to bovine serum albumin prepared in the rabbit was determined as 1:4069 in the radioimmunoassay, whereas according to the invention a sensitivity of 1:32788 can be obtained. Thus, the sensitivity is increased almost 8 times. Other conventional determination methods were much less sensitive than radioimmunoassay. Thus, the following antibody titres were obtained with known assays:

| in the nephelometer | 1:16 |
|---|---|
| in the immunodiffusion test | 1:64 |
| in the complement fixation reaction | 1:828 and |
| in ELISA | 1:512. |

The particular advantages of the invention are that the chemiluminescing labelling substance used can be bonded particularly easily to a reactant in a serological reaction, namely in the form of antigens and antibodies or bonding proteins. In addition, it is itself particularly simple and is unobjectionable for persons working with the process of the invention. The conjugates or complexes prepared with it are relatively stable, which is advantageous for performing the process.

The result obtainable on the basis of the invention must be considered extremely surprising. This applies more particularly with respect to fluorescein and the indicated derivatives. Thus, fluorescein or its derivatives after bonding to one of the said reactants of an immunological or serological reaction has a much higher sensitivity than the corresponding unbonded compound. The number of emitted photons of the chemiluminescing conjugate or the chemiluminescing complex is approximately 1000 times higher than the number of photons emitted by the in each case unbonded substance. In this connection, it is important that in Journal of Physical Chemistry, Vol.78, No.17, pp.1681–1683, 1979 express reference is made to the fact that for obtaining a measurable photon yield, it is necessary to use a disporportionately large quantity of fluorescein or fluorescein isothiocyanate. This has discouraged the Experts from previously using fluorescein or its derivatives for performing serological assays on the basis of a chemiluminescence measurement.

The invention is described in greater detail hereinafter relative to specific examples.

EXAMPLE 1

Determination of the detection limits of pure fluorescein isothiocyanate (FITC) and determination of the detection limit of an FITC conjugate For determining the detection limit of pure FITC, 1 mg of FITC was dissolved in 10 ml of distilled water and then the extinction of a 1:100 dilution was measured in the photometer at 495 nm. Then, ten dilutions (steps of 5) were prepared from the starting solution and in each case 20 µl thereof were measured in a commercial photometer. At the start of the measurement, 100 µl of an NaOCl solution (approx. 15 g of free chlorine/liter) were injected into the sample to be measured. The results of the series of measurements are given in the following tabulations:

| FITC quantity in ng/ml | Measured photons/sec. |
|---|---|
| 20,000 | 18,018 |
| 4,000 | 8,230 |
| 800 | 2,372 |
| 160 | 610 |
| 32 | 368 |

The blank reading of the apparatus for measurements without FITC was max. 360 photons/sec. under these conditions, so that the detection limit for pure FITC was 32 ng/ml.

For determining the detection limit of protein-bonded FITC, FITC was bonded to goat's immunoglobulin G according to the method of B. T. Wood, S. H. Thomson and G. Goldstein, described in Journal of Immunology, 95, 1964, p.225.

The extinction of the thus prepared chemiluminescing conjugate was also measured in the photometer at 495 nm, thereby determining the bound FITC quantity. This was again followed by 10 dilutions and the chemiluminescence of a 20 µl sample of each dilution was measured. The results of this series of measurements are given in the following tabulation:

| FITC quantity in ng/ml | Measured photons/sec. |
|---|---|
| 1,000 | 558,666 |
| 200 | 113,688 |
| 40 | 35,574 |
| 8 | 9,810 |
| 1.6 | 3,742 |
| 0.32 | 1,372 |
| 0.064 | 708 |
| 0.0128 | 360 |

The detection limit for the FITC protein conjugate was consequently 0.064 ng/ml. Thus, FITC conjugates are very suitable for the detection of antigens, antibodies or their complexes in a serological reaction by means of chemiluminescence.

EXAMPLE 2

Detection of antibodies against bovine serum albumin (BSA) in a rabbit serum

BSA was adsorbed on a flexible microtitre plate. The BSA was dissolved in a quantity of 0.1 mg/ml in a solution buffered with a sodium carbonate buffer to the pH value of 9.6. In each case, 100 µl of this were pipetted into a cup of the microtitre plate. The plate was then incubated for 16 hours at 4° C. After removal by suction and washing the plate three times with a phosphate-buffered salt solution with a pH value of 7.4 containing 1% sorbimacrogol laurate (cf Römpp's Chemielexikon, 7th edition, 1967, Vol. 6 p.3711, left-hand column under T20) a dilution series of the rabbit serum was introduced into the cups and incubated for 90 minutes at 37° C. After removal by suction and again washing the plate 3 times each cup was incubated with 100 µl of an FITC-labelled anti-rabbit serum (90 min. at 37° C.). After again washing 3 times, the individual cups were cut out and the chemiluminescence was measured in a commercial photometer. On this occasion, the chemiluminescence was brought about by adding 100 μl $H_2O_2$ (30%) and 100 μl chloramine (79 mg/ml). The results of the measurement are given in the attached graph. The numerical values on the ordinate give the number of measured photons whilst the numerical values on the abscissa express the degree of dilution of the rabbit hyperimmunoserum. The blank reading is a value determined in a special way. Thus, average blank readings X were determined from a number of blank readings and to the average blank reading was added the product of $2.58 \times \delta$, the factor $\delta$ representing the standard deviation. The graph shows that the boundary titre of rabbit serum is approximately 1:32788. In the solid phase radioimmunoassay the same rabbit serum had a boundary titre of 1:4096 and in ELISA a boundary titre of 1:512.

What is claimed is:

1. A process for the quantitative or qualitative determination of antigens, antibodies, and their complexes by means of a chemiluminescing labelling substance excited or activated for chemiluminescence by an analytical reagent, which comprises the steps of:
   (a) forming a chemiluminescing complex by
      (i) forming an antigen/antibody complex by means of a serological reaction;
         treating said antigen/antibody complex with a chemiluminescing conjugate containing a chemiluminescing labelling substance in the form of a chemiluminescing triphenylmethane dye coupled to an antigen, antibody or antigen/antibody complex to give said chemiluminescing complex; or
      (ii) directly forming said chemiluminescing complex by means of a serological reaction between said chemiluminescing conjugate and an antigen or antibody;
   (b) separating said chemiluminescing complex;
   (c) adding an exciting analytical reagent selected from mixtures of $H_2O_2$ with a chloramine; and
   (d) measuring the chemiluminescence resulting from step (c).

2. A process according to claim 1, wherein a solid phase assay is used.

3. A process according to claim 1, wherein the chemiluminescence is measured in an aqueous medium.

4. A process according to claim 1, wherein the chemiluminescence measurement is performed in a basic medium.

5. A process according to claim 1, wherein fluorescein isothiocyanate or fluorescein isocyanate is used as the chemiluminescing labelling substance.

6. A process according to claim 1, wherein a hepatitis B antigen is identified.

7. A process according to claim 1 or 2, wherein a sandwich assay is used.

* * * * *